(12) United States Patent
Ellsworth

(10) Patent No.: US 8,348,066 B2
(45) Date of Patent: Jan. 8, 2013

(54) FLOATING DISK FOR SEPARATING BLOOD COMPONENTS

(75) Inventor: James R. Ellsworth, Marshfield, MA (US)

(73) Assignee: Harvest Technologies Corporation, Plymouth, MA (US)

( * ) Notice: Subject to any disclaimer, the term of this patent is extended or adjusted under 35 U.S.C. 154(b) by 0 days.

(21) Appl. No.: 12/746,387

(22) PCT Filed: Dec. 8, 2008

(86) PCT No.: PCT/US2008/013481
§ 371 (c)(1),
(2), (4) Date: Oct. 21, 2010

(87) PCT Pub. No.: WO2009/073232
PCT Pub. Date: Jun. 11, 2009

(65) Prior Publication Data
US 2011/0036786 A1    Feb. 17, 2011

Related U.S. Application Data

(60) Provisional application No. 60/996,840, filed on Dec. 7, 2007.

(51) Int. Cl.
*B01D 21/26* (2006.01)
(52) U.S. Cl. ........ 210/516; 210/518; 210/787; 210/789; 210/800; 436/177; 422/527

(58) Field of Classification Search .................. 210/787, 210/789, 800, 516, 518; 422/527; 436/177
See application file for complete search history.

(56) References Cited

U.S. PATENT DOCUMENTS

| | | |
|---|---|---|
| 4,152,270 A | 5/1979 | Cornell |
| 5,269,927 A | 12/1993 | Fiehler |
| 2006/0032825 A1 | 2/2006 | Ellsworth et al. |
| 2006/0151384 A1 | 7/2006 | Ellsworth et al. |
| 2011/0278233 A1* | 11/2011 | Ellsworth ............. 210/782 |

* cited by examiner

*Primary Examiner* — David A Reifsnyder
(74) *Attorney, Agent, or Firm* — Clark & Brody

(57) ABSTRACT

A floating separating element for use in centrifugal separation of components of a physiological fluid comprises a positioning part and a separating part, where the positioning part is designed to automatically assume a position in a supernatant and a separating part is positioned at a desired location with respect to the interface between the supernatant and heavier components. In preferred embodiments the physiological fluids are blood or bone marrow aspirate, and the heavier components comprise red blood cells. The positioning part comprises the majority of the mass of the separating element and is thin so that differences in the position of the separating element with respect to the interface are small compared to differences in the densities of the separated compoments, particularly the component comprising red blood cells. A method allows red blood cells to move the separating element during decanting to ensure complete decant of the supernatant.

16 Claims, 8 Drawing Sheets

(a)     (b)

FLOATING DISK FOR SEPARATING BLOOD COMPONENTS

This application is the national stage entry of International Application Number PCT/US2008/013481, filed Dec. 8, 2008, which was published in English, and claims priority of U.S. Provisional Application No. 60/996,840, filed Dec. 7, 2007.

TECHNICAL FIELD

This invention relates to the art of fractionation of physiological fluids. In particular, the invention relates to the art of fractionation of blood and bone marrow aspirate by centrifugation.

BACKGROUND

Blood is commonly separated into its components by centrifugation. This may be done for many reasons, one of which is to obtain a selected component for use in treating a patient. For example, as disclosed in U.S. Pat. No. 6,398,972 (Blasetti) blood is separated into components by centrifugation to obtain platelet rich plasma, which is used in the autologous treatment of a patient. In this system, the whole blood is placed in one chamber of a processing unit, and the platelets and plasma are decanted to a second chamber after a first centrifugal spin. Then, subjecting the processing unit to a second centrifugal spin separates the platelets from the plasma. It is important to ensure that the platelets, as well as other desired components, such as white blood cells, are separated from the red blood cells in the first spin and decanted with the plasma while the red blood cells remain in the first chamber.

Blood, a physiological fluid, comprises a suspension of particles in a fluid, and includes principally plasma, red blood cells, platelets, and white cells, as well as many others. The density of plasma is generally about 1.020, and the density of platelets is about 1.040. The density of red blood cells varies between 1.07 to 1.09 depending on the age of the cell and other factors. The density of white cells lies between that of platelets and red cells. In practice, a "layer" will not be of purely one type of cell and may contain several types of cells. Thus, it is the usual practice to refer to the average density of a layer that is principally of one cell type but contains other cell types. For example, after centrifugation, the "plasma layer" will be principally plasma but will contain other cells, such as platelets and red blood cells, which raise the average density of the layer by an amount that depends on their proportions in the layer.

Another known system (U.S. Pat. No. 7,077,273) maintains separation between a supernatant and red blood cells by use of a separating element in the container of a physiological fluid, such as blood, subjected to centrifugation to assist in ensuring that the red blood cells remain in a chamber as the plasma, platelets and other components are transferred, as by decanting, to a second chamber. In early embodiments, a separating element was fixed in position in the first chamber at the expected location of the boundary between the red blood cells and the other components. That structure was found to be less than optimal because the actual location of the boundary between plasma and red blood cells is a function of several variables, such as the hematocrit of whole blood (i.e., the percentage of blood that comprises red blood cells), and the duration and G-force of the centrifugation. Yet another factor that affects the actual location of the boundary and the average density of the layers is the sedimentation rate of the components, which is affected by numerous factors, including the tonicity of the anticoagulant or other solutions that crenate, or swell, the cells, the age of the red blood cells (older cells are more dense), the age of platelet (younger cells are more dense), the size of the cells (large white blood cells sediment faster than smaller cells of equal density), the rouleau of red cells, and the viscosity of the plasma.

Separating elements designed to float in the physiological fluid are known, these elements being configured to float at or near the boundary between red blood cells and the desired supernatant elements. One such floating element shown in U.S. Pat. No. 7,077,273 is in the form of a disk designed, by its configuration and density, to position a surface just below the interface between red blood cells and the buffy coat (white blood cells and platelets). In that design, however, the focus is on the density of the red blood cell layer in the region of the interface with the buffy coat. While this design has proven successful, the desire for increases in the proportion of the target components to be recovered from the fluids (e.g., platelets and/or stem cells) that are obtained from a wide variety of patients, including those with diseases affecting the sedimentation rate of the cellular components, indicates a need for continued improvement.

Analysis of the fluid dynamics of centrifugal separation of the components of physiological fluids such as blood has shown that the density of the red blood cell layer that develops during centrifugation is difficult to determine with precision due to the factors discussed above affecting the sedimentation rate of the red blood cells. The actual density of the red blood cell layer depends on the proportion of red blood cells and other components, principally plasma, in the layer. Thus, if a particular patient has any of a number of conditions that reduce the sedimentation rate of the cellular components, the actual density of the red blood cell layer will be less than expected because it will have a larger portion of plasma. In that instance, the actual position of a floating disc designed on the basis of an expected density of the red blood cell layer will not be the expected position.

Because the layer of the desired cells, such as platelets and bone marrow stem cells, after centrifugal separation is generally very thin, an error in the position of the separating element may affect the recovery rate significantly. That is, an error in the placement of the separating element on the order of the thickness of the layer of desired cells could result in differences in the recovery rate by as much as fifty percent.

SUMMARY OF THE INVENTION

Applicant has discovered that while the actual density of the red blood cell layer is difficult to predict due to variations in sedimentation rates and the consequent proportion of less-dense plasma in the layer, the density of the plasma supernatant is reasonably predictable. Further, the density gradient at the boundary between the plasma layer and the red blood cell layer is relatively steep even though the density of the red blood cell layer itself is quite variable. The density of the red blood cell layer can vary from 1.05 to 1.8, and the density of the plasma layer can vary from 1.023 to 1.028. This indicates that the densities of the red blood cell and plasma layers vary, but that the variation in the density of the plasma layer is much less than that of the red blood cell layer.

Moreover, applicant has discovered that a majority of the desired components, such as platelets, white blood cells, and stem cells, are generally found in a thin layer at the interface and dispersed just below the interface, even in those instances where the density of the red blood cell layer is lower due to the presence of a greater proportion of plasma.

Thus, in accordance with one aspect of the invention, a floating separating element is configured to assume a position that is more dependent on the density difference between the plasma layer and the red blood cell layer than on the density of the desired layer of cells, such as platelets or white cells. In a preferred embodiment, the average density of the separating element is slightly greater than that of the plasma whereby it will sink in the plasma to a position in the vicinity of the boundary between the plasma and the red blood cells. The separating element also comprises, in essence, a positioning part and a separating part oriented below the positioning part. The distance between the positioning part and the separating part is determined by the expected position of the target cells with respect to the expected position of the positioning part with respect to the plasma-red blood cell interface. As will be explained below, the positioning part is preferably thin and comprises the majority of the mass of the overall separating element. Because the positioning part is designed to float partly in the plasma layer and partly in the RBC layer, the separating part may essentially form the bottom surface of the positioning part and provide a separating surface just below the interface.

Because the desired physiological components, e.g., platelets, stem cells, and white blood cells, are denser than plasma but less dense than red blood cells, they will form a layer essentially at the interface between the plasma and the red blood cells after centrifugation. In practice, however, the boundaries between layers are diffuse, with some red blood cells being found in the white cell "layer" and other layers (e.g., platelet or bone marrow cell), and vice versa. This diffusion means that the thickness of the layer of cells between the plasma and red blood cells varies depending on the portion of the other cells that are present in that "layer." Thus, to ensure recovery of the desired cells, the separating part must extend far enough below the plasma layer and into the red blood cell layer to be below the major part of the layer containing the desired cells so that most of these cells will be transferred.

Because the layer of desired cells is thin, errors in placement of the separating component are significant. While one solution might be to place the separating component much further below the interface than necessary, this often results in decanting too many red blood cells, which interferes with subsequent processing and results in an inferior product. Thus, an important aspect of the present invention is to control the position of the separating part below the interface to ensure collection of the desired cells while limiting the number of red blood cells collected.

In accordance with the invention, the separating part is connected to the positioning part and may be spaced from it by a predetermined distance whereby the positioning part will "push" the separating part into the red blood cell layer by a distance sufficient to ensure recovery of the desired cellular fractions at the interface between the plasma layer and the red blood cell layer. Because these components are found in the thin layer near the boundary, the invention provides the separating part at a fixed distance below the positioning part. In the preferred embodiment, the mass of the positioning part is more than about 65% and as much as about 80% of the total mass of the separating element to ensure that the positioning part is located close to the interface and capable of pushing the separating part below the interface by the desired distance.

In accordance with preferred specific features of the invention, the positioning part is a thin disk with a central hole to allow passage of the fluid as it moves in the processing tube having the physiological fluid. The periphery of the positioning part is preferably configured to engage the wall of the processing tube to ensure that the separating element floats freely in the fluids held in the tube without tipping. In a preferred embodiment, the periphery of the positioning part comprises several legs that extend upward from the body of the positioning part and engage the inner wall loosely to cooperate with the separating part to maintain the separating element upright and freely floating. The legs are thin so that the majority of the mass of the separating element remains in the positioning disk.

In accordance with another feature of the invention, the thickness of the positioning part is made to be small such that it minimizes the difference between its vertical positions with respect to the interface for the maximum and minimum expected densities of the plasma and red blood cell layers. This latter feature utilizes the phenomenon that for an element floating between two fluid layers the relative proportion of the floating element in one layer and in the other layer is determined by the relative densities of the layers. Configuring the separating element to include a positioning part and a separating part where the majority of the mass is in a thin positioning part minimizes the vertical difference between the locations of the separating part from the interface. This allows the layer of interest to be transferred, as by decanting, while minimizing the amount of other cells, such as red blood cells also transferred.

An object of this invention is to provide a separating element that floats near an interface between two components with the majority of its mass in a supernatant layer.

A further object of this invention is to provide a separating element that floats near an interface between a supernatant and red blood cells where the majority of the mass of the element remains in the supernatant layer and a smaller part extends into the red blood cell layer.

A still further object of the invention is a separating element that more accurately assumes a position with respect to an interface between layers of components of a physiological fluid.

A yet further object of the invention is a separating element having a majority of its mass in a thin portion of the separating element that is positioned in a supernatant.

DETAILED DESCRIPTION OF THE INVENTION

Figure 1:
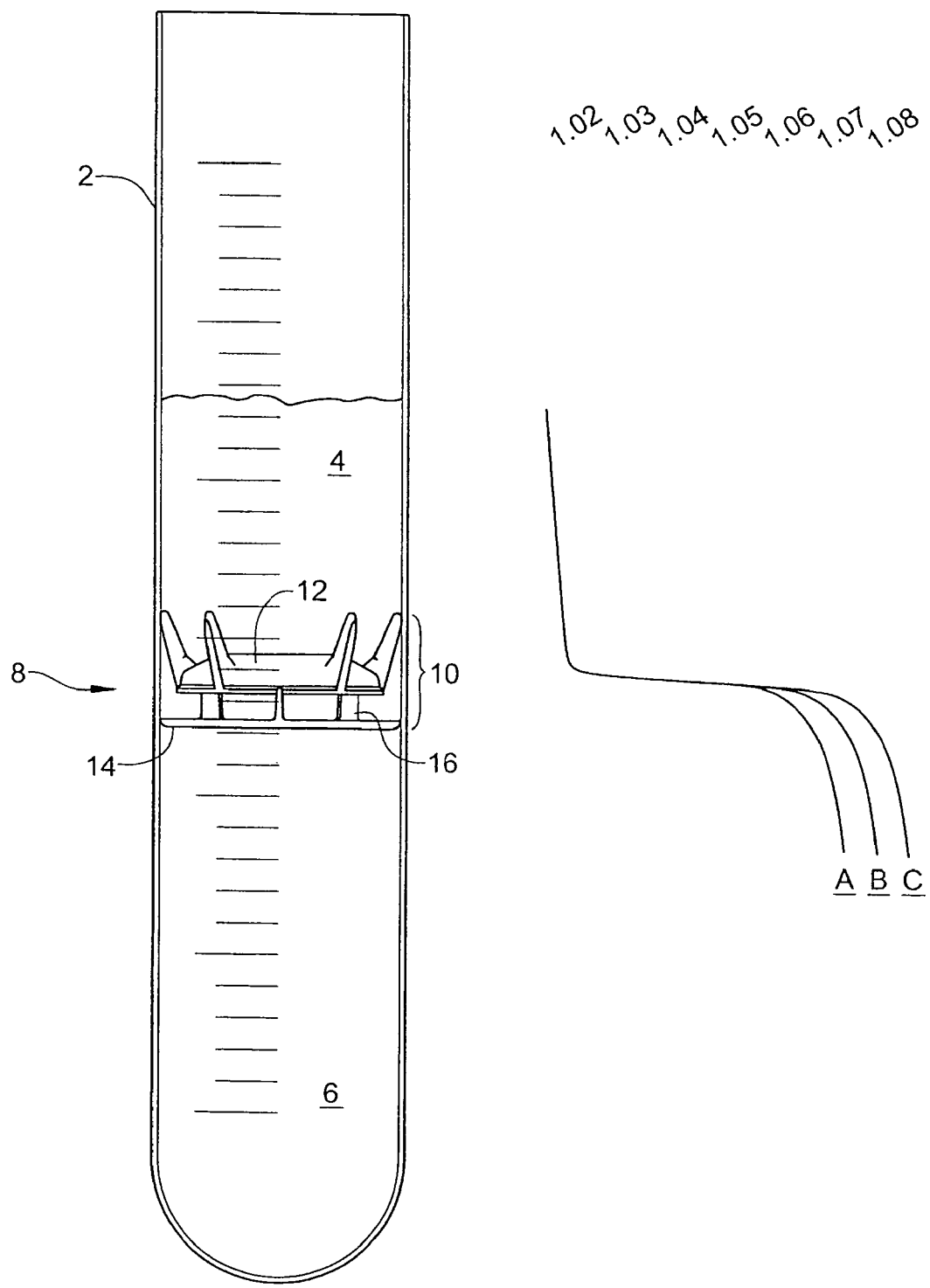
FIG. 1a is a schematic side view of a processing tube illustrating the invention.
FIG. 1b is a graphical illustration of the density profile of a physiological fluid in the processing tube of FIG. 1a after subjecting it to centrifugation.

With reference to figure 1a, a processing tube 2 has a physiological fluid therein. The processing tube 2 is illustrated as a simple cylindrical tube, but it will be appreciated that it can take any of various shapes. In a preferred embodiment, the processing tube 2 is one chamber of a two-chamber processing disposable such as that shown in U.S. Pat. No. 6,398,972. Alternatively, the processing tube 2 is part of a syringe arranged to express the separated components through one end of the syringe or to separate the supernatant in other ways. The processing tube is typically cylindrical whereby a circular floating disk of fixed diameter is freely movable in the tube to assume a location at the interface between components to be separated. Other configurations utilizing the principles of the invention are possible.

The physiological fluid in the processing tube 2 of FIG. 1a is shown after it has been subjected to centrifugation to separate the several components according to their densities. For example, the fluid might be whole blood after it has been subjected to a "soft spin," which separates less-dense platelet rich plasma 4 from more-dense red blood cells 6. The interface 8 between these components is generally not well defined and includes several components of particular interest, such as white blood cells and other nucleated cells. Alternatively, the fluid could be bone marrow aspirate in which case cells at the interface could be stem cells.

The graph of FIG. 1b illustrates the densities of the various components along the height of the processing tube 2. The density profiles for three different patients are illustrated as curves "A," "B," and "C."

It will be appreciated from the graph of FIG. 1b that the density of platelet rich plasma varies from 1.023 to about 1.028 for all patients, while the density of red blood cells varies from about 1.07 to about 1.09. The reasons for the variation in the density of the red blood cells themselves are many, as discussed above, and because sedimentation rates vary from patient to patient, the density of the red blood cell layer for any given centrifugation protocol varies in proportion to the plasma remaining in that layer. These variations make it particularly difficult to predict the density at the interface 8 or to position a separating element based on that density or that of the red blood cells.

Applicant has discovered, however, that the physical thickness of the interface is comparatively less variable than the density. That is, the layer of desired cells is essentially the top of the interface, and its thickness is less variable than the position of the interface in the tube 2. Thus a floating separating element is provided that sinks in the plasma and assumes a position floating in the plasma and red blood cells that is always close enough to the interface that a separating part of the separating element is always within a desired distance of the interface to allow the desired components to decant without also decanting an excessive number of red blood cells. One embodiment of such a floating separating element is illustrated in FIG. 1a, and additional embodiments are illustrated in FIGS. 2 through 5.

With reference to FIG. 1a, a floating separating element 10 in accordance with the principles of the invention is illustrated. This separating element generally comprises two parts, a first of which is a positioning part 12 and the second of which is a separating part 14. The two are preferably attached to each other by a connection 16 that provides a fixed distance between the two parts, but the connection 16 is alternatively adjustable to separate the two parts by a distance that can be varied. The density of the positioning part 12 is such that it will sink in the plasma 4 whereby the separating part will be pushed into the red blood cell layer. In the preferred embodiment, the positioning part is made of plastic having a density in the range of from about 1.047 to about 1.075 and preferably about 1.055. In preferred embodiments the positioning part may be made of Dow 666, having a density of about 1.047 or RTP 400, having a density of about 1.055.

Moreover, the positioning part is relatively larger than the separating part, whereby the location of the separating part is determined essentially by the location of the positioning part. Preferably, the mass of the positioning part is at least two times that of the separating part. In a particular embodiment, the mass of the positioning part is about 0.8 of the total mass of the separating element 10. Because the relative mass of the positioning part is large, the separating part 14 can be viewed as being held in the desired part of the interface by the positioning part 12 even though the density of the separating part itself is preferably less than that of the red blood cells.

The distance between the positioning part 12 and the separating part 14 is predetermined in accord with the particular characteristics of the fluid, such as whether it is whole blood or bone marrow aspirate, and the particular configuration of the positioning and separating parts.

Figure 2:
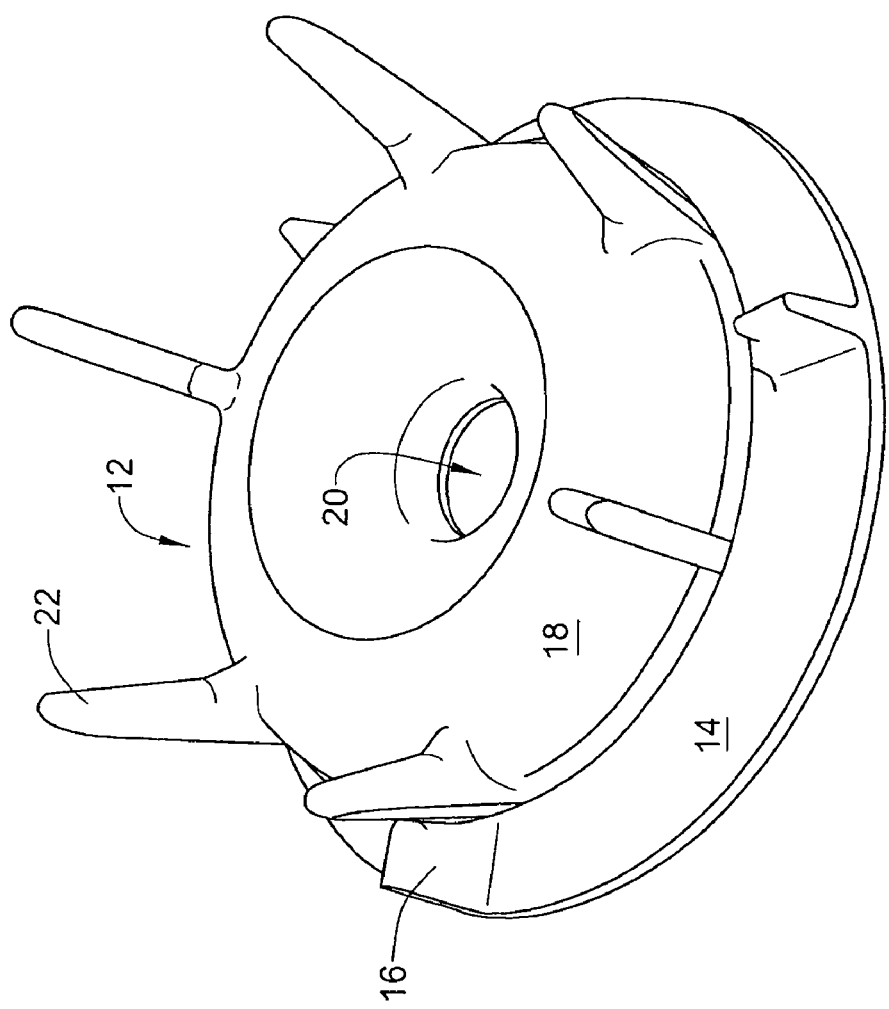
FIG. 2 is a perspective of a preferred embodiment of a separating element according to the invention.

FIG. 2 illustrates a preferred embodiment of the separating element. The positioning part 12 comprises a body 18 of generally annular configuration with a central hole 20. Several legs 22 extend upward from the periphery of the body 18. The body 18 is preferably thin such that it will assume a location close to the interface during centrifugation. The body 18 also comprises the majority of the mass of the floating separating element 10 so that its characteristics are the primary factor in the position the separating element in the fluids. By making the body 18 thin, the vertical difference between its positions with respect to the interface is small when compared to differences in the characteristics of the fluids obtained from various patients, as described above. This feature of the invention will now be explained in more detail.

In a known analysis of buoyancy, a floating object displaces a volume of fluid in which it floats that is equal to the weight of the object. Thus, the following relationship obtains:

$$v(sub)\rho(fluid) = v(obj)\rho(obj)$$

where:
  v(sub) is the submerged volume of the floating object,
  ρ(fluid) is the density of the fluid in which the object is floating,
  v(obj) is the total volume of the floating object, and
  ρ(obj) is the density of the floating object.
Thus, the ratio of the submerged volume to the total volume is proportional to the ratio of the density of the object to the density of the fluid, as:

$$v(sub)/v(obj) = \rho(obj)/\rho(fluid)$$

From this relationship it can be seen that for any given object, the submerged volume of the floating object is a function of the density of the fluid in which it floats. Thus, with reference to the present invention, wherein the density of the fluids is not controllable, for the reasons described above, it may be noted that the volume of the floating element 10 that is submerged in the red blood cells is not controllable.

In the more complicated environment of a centrifuge where the separating element 10 floats in plasma and red blood cells, the following relationship is more accurate:

$$\rho(rbc) - \rho(sc)/\rho(sc) - \rho(plasma) = m(plasma)/m(rbc)$$

Where:
$\rho(rbc)$ is the density of the red blood cell layer'
$\rho(sc)$ is the density of the separating element,
$\rho(plasma)$ is the density of the plasma layer,
$m(plasma)$ is the mass of the separating element in the plasma layer, and
$m(rbc)$ is the mass of the separating element in the red blood cell layer.

It will be appreciated that a conclusion may be drawn from the above formulation that is similar to that drawn from the earlier, but more basic formulation, namely, that the proportion of the separating element in the plasma layer and the proportion in the red blood cell layer is a function of the densities of the layers and the separating element.

While the position of the separating element at the interface is not controllable, because the actual densities of the layers are not controllable, a separating element configured according to the invention ensures that the distance between the maximum and minimum positions possible provides acceptable results. This is achieved by placing most of the mass of the separating element in the positioning part and by making the positioning part thin. The effects of this are illustrated in FIG. 3.

Figure 3:
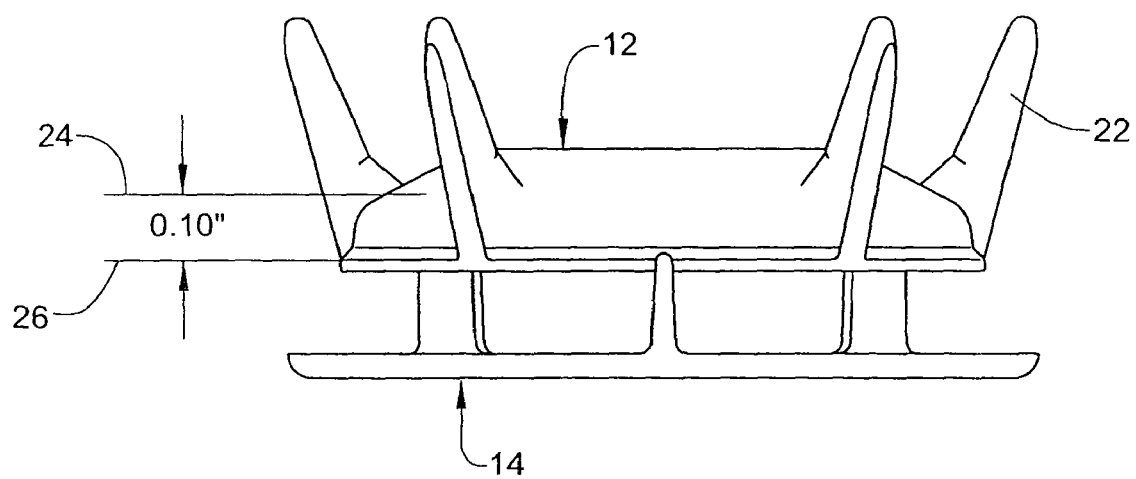
FIG. 3 is a side view of the separating element of FIG. 2.

FIG. 3 is a side view of the separating element shown in FIG. 2 illustrating the difference in its position for different average densities of the plasma layer and the red blood cell layer.

This difference has been calculated in accordance with the above formulas and has been found to be substantially accurate in testing. With reference to FIG. 3, line 24 illustrates the position of the interface between plasma and red blood cells when the average density of the plasma layer is 1.025, the average density of the red blood cell layer is 1.05, and the density of the separating element is 1.047. Line 26 illustrates the position of the interface for the same separating element and plasma density but where the average density of the red blood cell layer is 1.07. Thus, the separating element floats higher when the average density of the red blood cell layer is greater, but the vertical difference between the two positions of the separating element is only about 0.10 inch. Because in the embodiment shown, the separating part is connected to the positioning part for movement with it, the same vertical difference in position applies to the separating part 14.

Accordingly, by application of the principles of the invention, the difference in vertical position of the separating part 14 from the interface can be made to be about 0.10 inch for a relatively large variation in the average density of the red blood cell layer, which is typical of that experienced in practice. This allows one to position the separating part with respect to the positioning part according to the cell layer to be recovered with the assurance that the error in its position will be less than, for example, 0.10 inch. In this example, the volume of cellular fluid above the separating part 14 is calculated to be about 4.8 cc when the RBC density is 1.055 and about 4.3 cc when the RBC density is 1.070. Thus, the difference is about 0.5 cc, which is quite small when compared with a known prior art floating disk, where the difference between the volumes of cellular fluid above the separating part for the same difference in RBC densities is about 4.1 cc of cellular fluid.

In the embodiment discussed above, the separating element 10 is designed to float in a cylindrical tube with 60 ml of physiological fluid and having a diameter of about 1.36 inches. Thus the diameter of the separating part 14 is slightly less than this, about 1.34 inches, to allow it to move in the tube, and the diameter of a circle encompassing the outer most surfaces of the legs is about 1.34 inches also, so the legs can provide the necessary stability. The volume of the positioning part 12 is about 2.56 cc, and the volume of the separating part is about 1.17 cc. The diameter of body 18 is about 1.12 inch, the diameter of hole 20 is about 0.24 inch, and the thickness of the body 18 is about 0.22 inch. The thickness of the separating part is about 0.05 inch.

Figure 4:
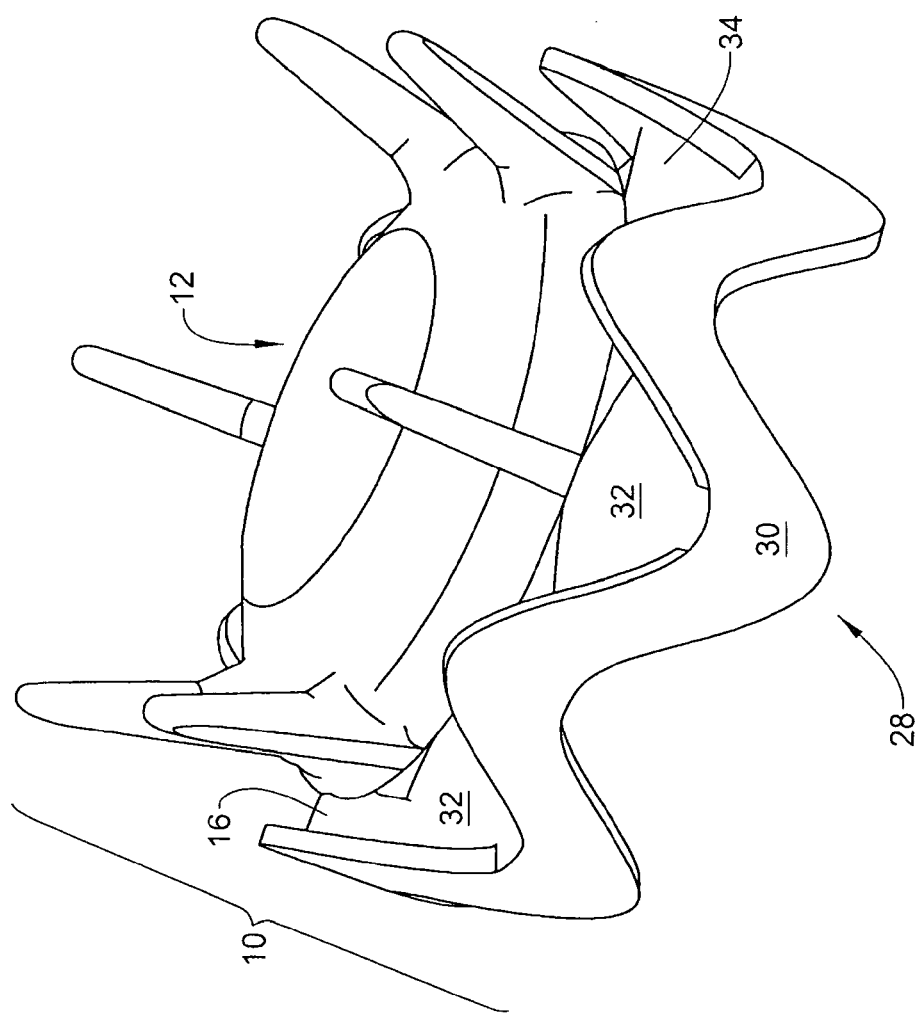
FIG. 4 is a perspective view of a second preferred embodiment of a separating element according to the invention.

FIG. 4 illustrates a second embodiment of a separating element 10 according to the invention. In this embodiment, the positioning part 12 is the same as shown in FIG. 2, but the separating part 28 is provided with a sinuous perimeter 30 and a central portion that includes radial valleys 32 when viewed from the upper surface, which are peaks when viewed from the bottom, and radial peaks 34, which are valleys when viewed from below. The volume of the separating part 28 in this embodiment is about 0.96 cc.

A primary advantage of the embodiment shown in FIG. 4 is that the sinuous shape of the separating part facilitates passage of cells and air past the separating part during centrifugation. Because the tube 2 typically contains air before blood is added, air trapped below the separating element before centrifugation must be allowed to flow upward during centrifugation. The valleys tend to accumulate air flowing upward or heavier cells flowing downward to pass the separating part by a funneling effect. In addition, the sinuous perimeter 30 of the separating part is of a thickness that it adheres to the side of the tube during decant and tends to wipe the side of the tube as the separating part 10 is pushed along the tube by red blood cells during decant, as will be described further below.

Figure 5:
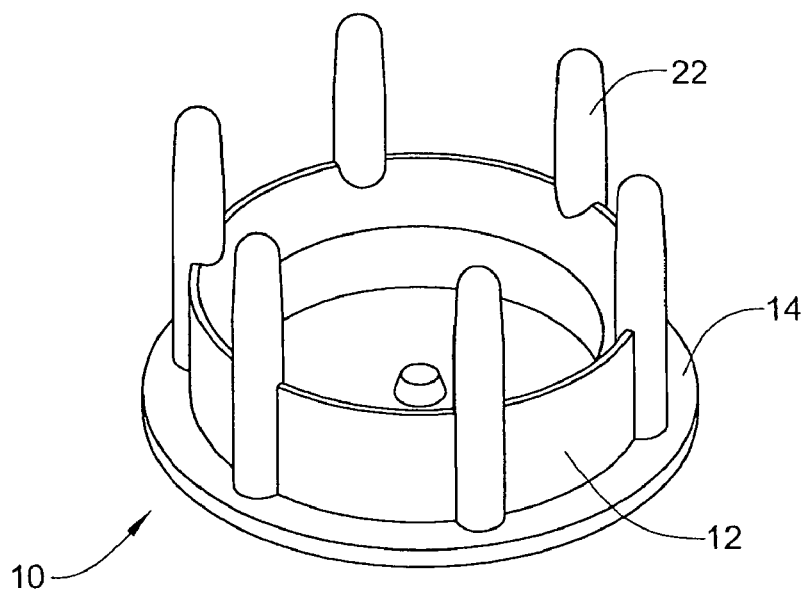
FIG. 5 is a perspective view of a third preferred embodiment of the invention.
Figure 6:
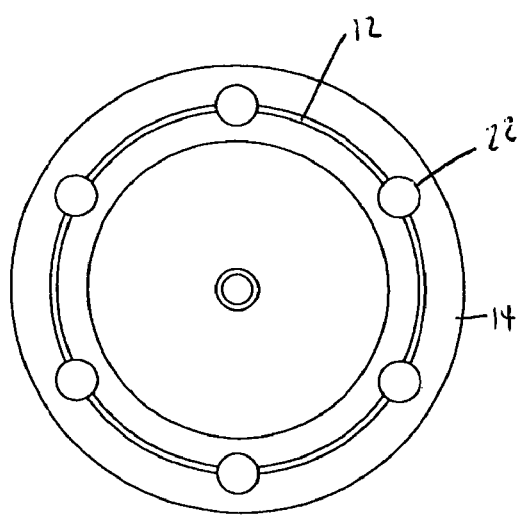
FIG. 6 is a top plan view of the third embodiment.
Figure 7:
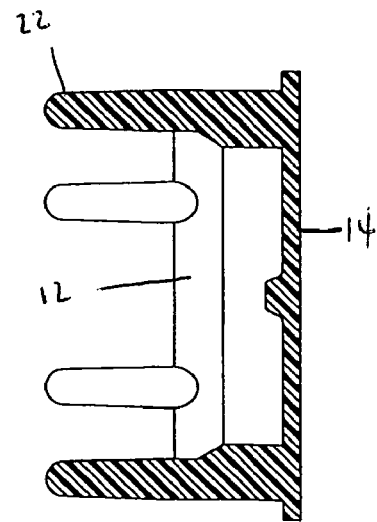
FIG. 7 is a vertical cross section of the third embodiment.

FIGS. 5 through 7 illustrate yet another embodiment of the invention wherein the distance between the positioning part 12 and the separating part 14 is reduced essentially to zero. In essence, the separating part in this embodiment is coextensive with the bottom of the positioning part but all other factors previously discussed remain the same.

Figure 8:
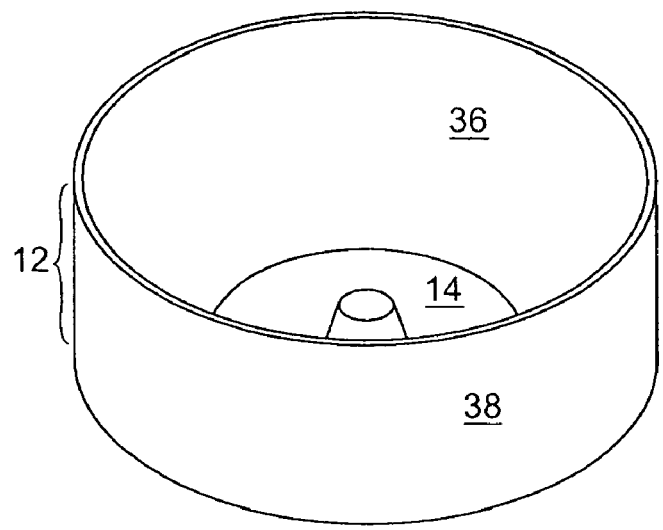
FIG. 8 is a perspective view of a fourth preferred embodiment of the invention.
Figure 9:
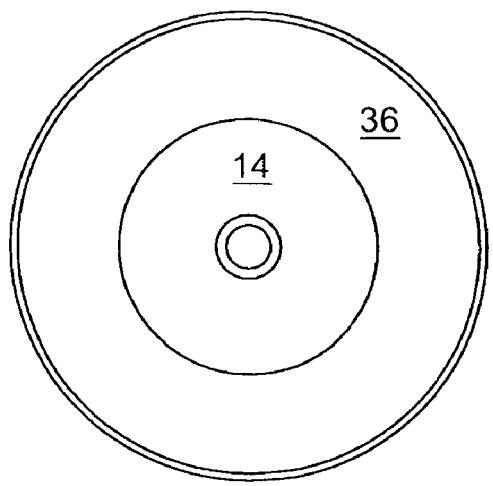
FIG. 9 is a top plan view of the fourth embodiment.
Figure 10:
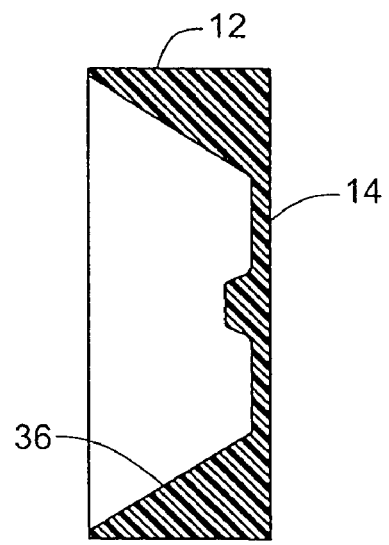
FIG. 10 is a vertical cross section of the fourth embodiment.

FIGS. 8 through 10 illustrate a still further embodiment similar to that of FIG. 5 where the mass distribution of the separating part is such that the objective of having the bulk of the mass in the positioning part is achieved. It will be appreciated that in this embodiment the inner wall 36 tapers toward the outer wall 38 whereby the sidewall becomes progressively thinner toward the top to perform the stabilizing function of the legs 22 of the other embodiments. Thus, the out wall 38 may be cylindrical while the inner wall 36 is conical. In this embodiment, the increase in mass toward the bottom is linear to provide a positioning part 12 as described, but it may be non-linear whereby an even greater percentage of the mass is positioned in a thin region.

Figure 11:
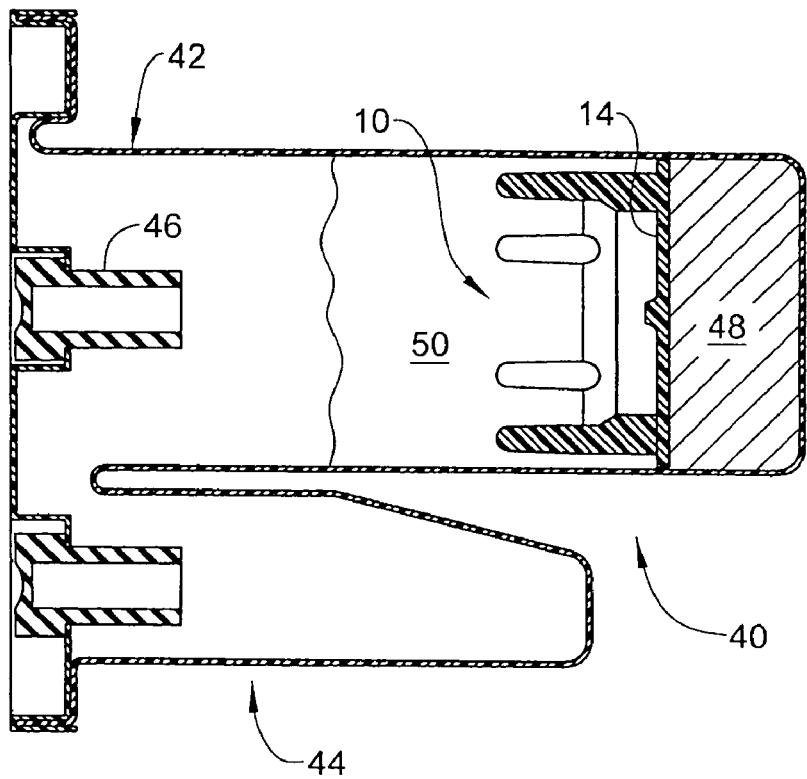
FIG. 11 is a vertical cross section of a processing unit illustrating the operation of a separating element in accordance with the invention during centrifugation.

FIGS. 11 through 14 illustrate a feature of the invention wherein the separating element 10 acts as a squeegee to increase the efficiency of decanting the plasma and the desired cellular components. FIG. 11 illustrates a processing unit in use with a separating element 10 as shown in FIG. 5. Processing unit 40 includes a first sterile chamber 42 for receiving blood, and a second sterile chamber for receiving plasma and cellular components decanted from the first chamber. The separating element 10 is placed in the first chamber during manufacture of the processing unit. Blood is injected into the first chamber by inserting a syringe needle (not shown) through an entry port 46. The processing unit with the blood therein is then placed in a centrifuge (not shown) and subjected to centrifugation to separate, in the case of whole blood, the red blood cells from plasma and other particularly desired cellular components including platelets and white blood cells. As described above, the floating separating element 10 will assume a position depending on the density of the fluids in which it floats. FIG. 11 illustrates the condition of the processing unit just at the end of the centrifugation when the majority of the red blood cells have migrated to a layer 48 below the separating part due to the centrifugal forces. The plasma is located in a layer 50 above the separating part 10, and other desired cellular components are located just above the separating element 14.

Figure 12:
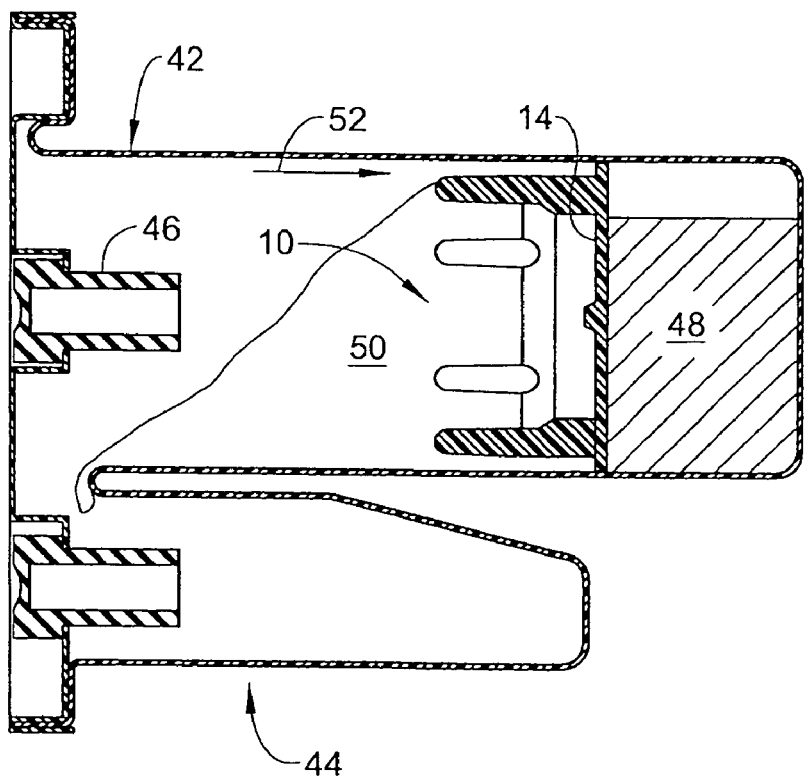
FIG. 12 illustrates the unit of FIG. 11 in an initial stage of decanting.

In the embodiment shown in FIG. 11, the separating element is configured such that it will tip enough in response to the pressure on its lower peripheral parts by the red blood cells that the upper part will allow air to flow past the separating element and into the part of the chamber having the red blood cells (i.e., the right-hand part in the figures). At the point in the operation illustrated in FIG. 11, the centrifugation is stopped, but the orientation of the processing unit is maintained, for example, by a mechanism described in U.S. Pat. No. 6,398,972. At this point, the plasma layer 50 begins to decant and flow into the second chamber 44. As the top of the plasma layer falls below the upper edge of the separating part 14, some air passes to the right side of the separating part, as viewed in FIG. 12. At the same time, the weight of the RBC layer 48 causes it to push the separating element 10 to the left. When the separating element moves to the left, the level of the RBC layer 48 decreases because of the larger width of the space between the separating element and the bottom of the chamber 42 and the constant volume of the RBC layer. This causes the RBC layer to apply a greater force to the bottom of the separating element than on the top, which in turn causes the separating element to tilt slightly backward (i.e., clockwise as seen in FIG. 12). This allows more air to enter at the top with the result that the RBC layer pushes the separating element further to the left.

Figure 13:
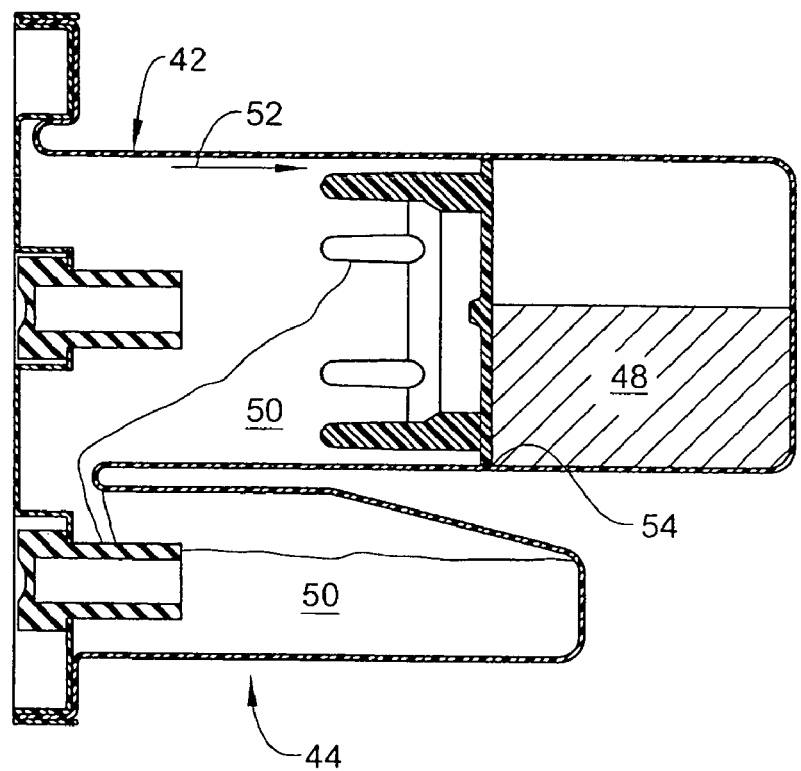
FIG. 13 illustrates the unit of FIG. 11 in a further stage of decanting.
Figure 14:
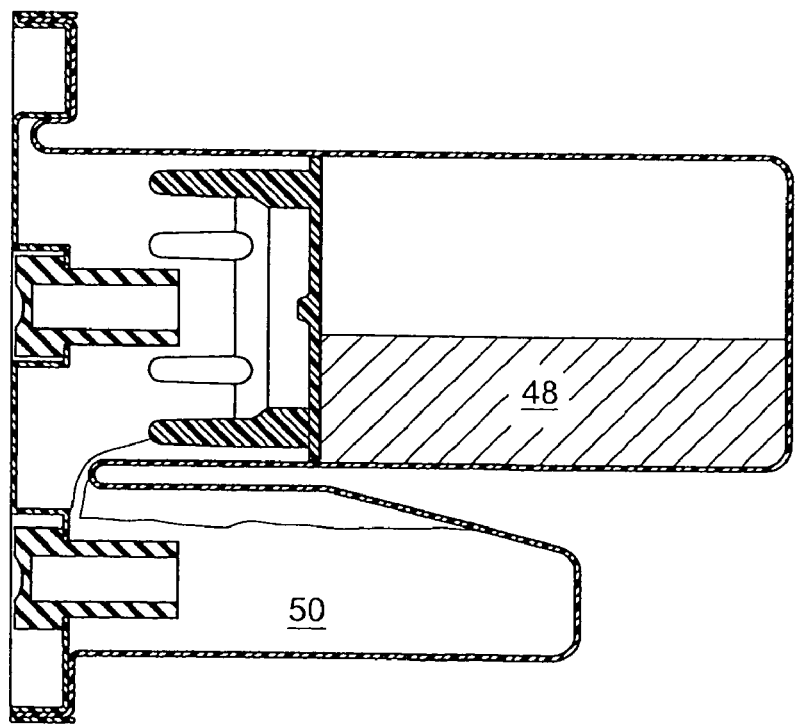
FIG. 14 illustrates the unit of FIG. 11 in a final stage of decanting.

FIGS. 13 and 14 illustrate the continued movement of the separating element to the left as a result of the forces applied by the RBC layer to the separating element. An important feature of this is that the bottom edge 54 of separating part 14 moves along the wall of the chamber 42 acting as a squeegee to ensure better collection of the layer 50 and decant of the layer 50 into the second chamber 44.

Modifications within the scope of the appended claims will be apparent to those of skill in the art.

I claim:

1. An article for ensuring separation of components of a physiological fluid comprising a first part configured to float in a first, lighter component of said physiological fluid and a second part spaced from said first part by a predetermined distance and configured to float in a second, denser component, wherein the mass of said first part is at least about 65% of the total mass of the article.

2. An article according to claim 1 wherein the mass of said first part is 65% to 80% of the total mass of the article.

3. An article according to claim 2 wherein the mass of said first part is about 68% of the total mass of the article.

4. An article according to claim 1 wherein said first part comprises a thin disk and a plurality of stabilizing legs for providing stability when said article floats within a tube.

5. An article according to claim 4 wherein said second part is a thin flat disc.

6. An article according to claim 4 wherein said second part is a thin disk forming a series of radially extending peaks and valleys.

7. An article according to claim 1 wherein said second part is a thin disk forming a series of radially extending peaks and valleys.

8. An article according to claim 1 wherein said first and second parts are contiguous.

9. An article according to claim 8 wherein said first part includes circumferential stabilizing legs for providing stability when said article floats within a tube.

10. An article according to claim 8 wherein said first part comprises an outer wall and an inner wall that tapers toward said outer wall.

11. An article according to claim 10 wherein said outer wall is cylindrical and said inner wall is conical.

12. An article according to claim 1 wherein said first and second parts are configured such that when the density of said lighter component is substantially constant, and the density of said second component varies by about two percent, the difference in position of said article with respect to an interface between said first and second components is less than about 0.10 inch.

13. An article according to claim 1 wherein said physiological fluid is blood and said second component comprises red blood cells.

14. An article according to claim 13 wherein said first component comprises platelets.

15. An article according to claim 1 wherein said physiological fluid is bone marrow aspirate and said second component comprises red blood cells.

16. An article according to claim 15 wherein said first component comprises stem cells.

\* \* \* \* \*